(12) United States Patent
Liang

(10) Patent No.: US 6,555,672 B1
(45) Date of Patent: Apr. 29, 2003

(54) GROWTH DIFFERENTIATION FACTOR PROMOTER AND USES THEREFOR

(75) Inventor: Li-fang Liang, Elkridge, MD (US)

(73) Assignee: MetaMorphix, Inc., Savage, MD (US)

( * ) Notice: Subject to any disclaimer, the term of this patent is extended or adjusted under 35 U.S.C. 154(b) by 0 days.

(21) Appl. No.: 09/354,409

(22) Filed: Jul. 15, 1999

Related U.S. Application Data

(60) Provisional application No. 60/092,865, filed on Jul. 15, 1998, and provisional application No. 60/123,270, filed on Mar. 8, 1999.

(51) Int. Cl.$^7$ ............................................. C07H 21/04
(52) U.S. Cl. .................. 536/24.1; 536/23.1; 435/235.1; 435/325
(58) Field of Search .................. 514/44; 435/320.1, 435/235.1, 325; 424/93.2, 93.21; 536/23.1, 24.1

(56) References Cited

PUBLICATIONS

Mullins et al. J Clin. Invest. 98(11): S37–40, 1996.*
Palmiter et al. Ann Rev. Genet. 20: 465–99, 1986.*
Cameron, ER. Molecular Biotechnology. 7: 253–265, 1997.*
Eck et al. "Gene Based Therapy" Chap 5, Goodman & Gilman's The Pharmacological Basis of Therapeutics. 9th Ed. pp. 77–101, 1995.*
Verma et al. Nature. 389: 239–242, Sep. 1997.*
Miller et al. FASEB J. 9: 190–199, Feb. 1995.*
Deonarain, MP. Exp. Opin. Ther. Patents. 8(1): 53–69, 1998.*
Crystal R.G. Science. 270: 404–410, 1995.*
McPherron et al. J Biol. Chem. 268(5): 3444–9, Feb. 1993.*
GenCore Accession No. AF093798, Daneau et al., Oct. 1998.*
GenCore Accession No. X24464, Georges et al., Jun. 1999.*
Dickman S. Gene mutation provides more meat on the hoof. Science. Sep. 26, 1997;277(5334):1922–3.
GenBank Accession No. AJ133580 for Sus scrofa partial myostatin gene.
GenBank Accession No. AF093798 for Sus Scrofa myostatin (gdf8) gene.
Gonzalez–Cadavid NF, et al., Organization of the human myostatin gene and expression in healthy mean and HIV–infected men with muscle wasting. Proc Natl Acad Sci U S A. Dec. 8, 1998;95(25):14938–43.
Grobet L, et al. A deletion in the bovine myostatin gene causes the double–muscled phenotype in cattle. Nat Genet. Sep. 1997;17(1):71–4.
Grobet L, et al. Molecular definition of an allelic series of mutations disrupting the myostatin function and causing double–muscling in cattle. Mann Genome. Mar. 1998;9(3):210–3.
Ji S, et al. Myostatin expression in porcine tissues: tissue specificity and developmental and postnatal regulation. Am J Physiol. Oct. 1998;275(4 Pt 2):R1265–73.
Kambadur R, et al. Mutations in myostatin (GDF8) in double–muscle Belgian Blue and Piedmontese cattle. Genome Res. Sep. 1997;7(9):910–6.
McPherron AC, et al. Regulation of skeletal muscle mass in mice by a new TGF–beta superfamily member. Nature. May 1, 1997;387(6628):83–90.
McPherron AC, et al. Double muscling in cattle due to mutations in the myostatin gene. Proc Natl Acad Sci U S A. Nov. 11, 1997;94(23):12457–61.
Murch SH, et al. Nutrition in inflammatory bowel disease. Baillieres Clin Gastroenterol. Dec. 1998:12(4):719–38.
Slack JM. Growth control: action mouse. Curr Biol. Aug. 1, 1997;7(8):R467–9.
Smith TP, et al. Myostatin maps to the interval containing the bovine mh locus. Mamm Genome. Oct. 1997;8(10):742–4.
Sonstegard TS, et al. Refinement of bovine chromosome 2 linkage map near the mh locus reveals rearrangements between the bovine and human genomes. Anim Genet. Oct. 1998;29(5):341–7.
Sonstegard TS, et al. Myostatin maps to porcine chromosome 15 by linkage and physical analyses. Anim Genet. Feb. 1998;29(1):19–22.
Szabo G, et al. A deletion in the myostatin gene causes the compact (Cmpt) hypermuscular mutation in mice. Mamm Genome. Aug. 1998;9(8):671–2.
Westhusin M. From mighty mice to mighty cows. Nat Genet. Sep. 1997;17(1):4–5.

* cited by examiner

*Primary Examiner*—Deborah Crouch
(74) *Attorney, Agent, or Firm*—Lahive & Cockfield, LLP; Jane E. Remillard; Maria Laccotripe Zacharakis

(57) ABSTRACT

GDF promoters (e.g., GDF-8 promoters) are described. Also described are methods of using the GDF promoters to regulate tissue-specific gene expression, and to identify compounds which regulate GDF expression.

14 Claims, 14 Drawing Sheets

-646
```
ACTAGTATCA TAATCTTAAC TTTTAATTCA GGTCTTCCTA ATTTTTATTT
TGATCATAGT ATTAGAATTG AAAATTAAGT CCAGAAGGAT TAAAATAAAA

TCCTAATTAC TTGGCACTAA AAATAATTTA ATACAACAAA TAAAAATATT
AFFATTAATG AACCGTGATT TTTATTAAAT TATGTTGTTT ATTTTTATAA

TTCTACTTCA AATACTTGCC TAAACAATAT AAAATCATTT TAGTTTTTGA
AAGATGAAGT TTATGAACGG ATTTGTTATA TTTAGTAAA ATCAAAAACT
                 -437
GGAAGTAATA TTTCATATTT TAAATATGTA GTATAAATTA AAATTGACTT
CCTTCATTAT AAAGTATAAA ATTTATACAT CATATTTAAT TTTAACTGAA

ATTTAAATTA CAATAAGAGT TGTGTGAGGA TTAGTAAGAT TTAAGTACAG
TAAATTTAAT GTTATTCTCA ACACACTCCT AATCATTCTA AATTCATGTC

TTTATATTAT TGCCAACATA GACTTTTGTT TTTCAAATGT CACAAATATC
AAATATAATA ACGGTTGTAT CTGAAAACAA AAAGTTTACA GTGTTTATAG
                                                -310
TTTTATTATT TGTAGATTTA TTTCTTTTAT GAAGTAGTCA AATGAATCAG
AAAATAATAA ACATCTAAAT AAAGAAAATA CTTCATCAGT TTACTTAGTC
           -286
CTCACCCTTG ACTGTAACAA AATACTGCTT GGTGACTTGG GACAGACAGG
GAGTGGGAAC TGACATTGTT TTATGACGAA CCACTGAACC CTGTCTGTCC
-246                                         -207
GTTTTAACCT CTGACAGCGA GATTCATTGT GGAGCAAGAG CCAATCATAG
CAAAATTGGA GACTGTCGCT CTAAGTAACA CCTCGTTCTC GGTTAGTATC

ATCCTGACGA CACTTGTCTC ATCTAAGTTG GAATATAAAA AGCCACTTGG
TAGGACTGCT GTGAACAGAG TAGATTCAAC CTTATATTTT TCGGTGAACC

AATACAGTAT AAAAGATTCA CTGGTGTGGC AAGTTGTCTC TCAGACTGTA
TTATGTCATA TTTTCTAAGT GACCACACCG TTCAACAGAG AGTCTGACAT
 -95
CATGCATTAA AATTTTGCTT GGCATTACTC AAAAGCAAAA GAAAAGTAAA
GTACGTAATT TTAAAACGAA CCGTAATGAG TTTTCGTTTT CTTTTCATTT
                                                  +1
AGGAAGAAAC AAGAACAAGA AAAAGATTA TATTGATTTT AAAATCATG
TCCTTCTTTG TTCTTGTTCT TTTTTCTAAT ATAACTAAAA TTTTAGTAC
```

Fig. 2

Box 1 sequence (CAAATG)

GAGCTTTCTTTTATGAAGTAGT[CAAATG]AATCAGCTCACCCTTG
       AAAGAAAATACTTCATCAGTTTACTTAGTCGAGTGGGAACCTCG

Box 3 sequence (GACAGC)

GAGCGTTTTAACCTCT[GACAGC]GAGATTCATTGTGGAGCAAGAG
       CAAAATTGGAGACTGTCGCTCTAAGTAACACCTCGTTCTCCTCG

4 - 10 copies of Box 1 or Box 3 double
stranded oligonucleotide sequences

```
         10        20        30        40        50        60
GTACAGTTTATATTAGTACACAGACTTCAATTTATCAAATGTCACATATATCTTTCATGA
CATGTCAAATATAATCATGTGTCTGAAGTTAAATAGTTTACAGTGTATATAGAAAGTACT 70        80        90       100       110       120
TTTGGGGATTTATTTCATTTATGAAGTAGTCAAATGAATCAGCTTGCCCTCGACTGTAAC
AAACCCCTAAATAAAGTAAATACTTCATCAGTTTACTTAGTCGAACGGGAGCTGACATTG 130       140       150       160       170       180
AAAATACTGCTTGGTGACTTGTGACAGACAGGGTTTTAACCTCTGACAGCGAGATTCATT
TTTTATGACGAACCACTGAACACTGTCTGTCCCAAAATTGGAGACTGTCGCTCTAAGTAA 190       200       210       220       230       240
GTGGAGCAGGAGCCAATCATAGATCCTGACGACACTTGTCTCCTCTAAGTTGGAATATAA
CACCTCGTCCTCGGTTAGTATCTAGGACTGCTGTGAACAGAGGAGATTCAACCTTATATT 250       260       270       280       290       300
AAAGCCACTTGGAATACAGTATACAGGACTCCCTGGCGTGGCAGGTTGTCTCTCGGACGG
TTTCGGTGAACCTTATGTCATATGTCCTGAGGGACCGCACCGTCCAACAGAGAGCCTGCC 310       320       330       340       350       360
TACATGCACTAATATTTCACTTGGCATTACTCAAAAGCAAAAAGAAGAAATAAGAACAAG
ATGTACGTGATTATAAAGTGAACCGTAATGAGTTTTCGTTTTTCTTCTTTATTCTTGTTC 370       380       390
GGAAAAAAAAAGATTGTGCTGATTTTTAAAATGATG
CCTTTTTTTTTCTAACACGACTAAAAATTTTACTAC
```

Fig. 7A

```
         10        20        30        40        50        60
TTCGGTATNTAATTTGCTGCCCAGGATTTNGNTGACAAAGGCAAACTGGNTTAANTTAAT
AAGCCATANATTAAACGACGGGTCCTAAANCNACTGTTTCCGTTTGACCNAATTNAATTA 70        80        90       100       110       120
AGGGTCCACACTTCAGTAATGAATTTTGATANTAAAGGTCCCAATAGTTAGCANTTATAG
TCCCAGGTGTGAAGTCATTACTTAAAACTATNATTTCCAGGGTTATCAATCGTNAATATC 130       140       150       160       170       180
TCACACGTGAACAAAATGTTTATTCNTGNTNACNTAGNACNTATCAGGAAAACCTATCAT
AGTGTGCACTTGTTTTACAAATAAGNACNANTGNATCNTGNATAGTCCTTTTGGATAGTA 190       200       210       220       230       240
GATTTTCTGAAATCTGAGCTGCTTAATGCACGTGAACTGTTGAACAGCATGGATTCCTCG
CTAAAAGACTTTAGACTCGACGAATTACGTGCACTTGACAACTTGTCGTACCTAAGGAGC 250       260       270       280       290       300
TGTTTGCAATGTATTTATAATGTATTTTTTCCCCTCCTCCTAACAGAAATCCCTCAGAA
ACAAACGTTACATAAATATTACATAAAAAAGGGGAGGAGGATTGTCTTTAGGGAGTCTT 310       320       330       340       350       360
TTTTCCTTGAGGTAGTACAAACTTTCAGCCACAATAGTGATAGAATCCTAAAGGAACCCT
AAAAGGAACTCCATCATGTTTGAAAGTCGGTGTTATCACTATCTTAGGATTTCCTTGGGA 370       380       390       400       410       420
AAAAGAGAGCTCTGCCTCAATTCATAGTCCAACTATGCGTTCAGTGTATATTTAAGAATG
TTTTCTCTCGAGACGGAGTTAAGTATCAGGTTGATACGCAAGTCACATATAAATTCTTAC 430       440       450       460       470       480
ATAGTGCTGTCTTCCAGCACTGCTGCCCATAGTACTTGGAAATATATCCTTTCAGTATGT
TATCACGACAGAAGGTCGTGACGACGGGTATCATGAACCTTTATATAGGAAAGTCATACA 490       500       510       520       530       540
GAAGACGTATCCTTTACGAAGCCACCATATAAATCAGTTCACCCTTGGCTGTAACCAAAT
CTTCTGCATAGGAAATGCTTCGGTGGTATATTTAGTCAAGTGGGAACCGACATTGGTTTA 550       560       570       580       590       600
GCTGTCTAGTGACTTGTGATCGACAGGGCTTTAACCTCTGACAGCTAGATTCATTGTTGG
CGACAGATCACTGAACACTAGCTGTCCCGAAATTGGAGACTGTCGATCTAAGTAACAACC 610       620       630       640       650       660
GACAACAACCAATCGTCGGTTTTGACGACATGAGCCTAATCAAAGTTGGAGTATAAAAGC
CTGTTGTTGGTTAGCAGCCAAAACTGCTGTACTCGGATTAGTTTCAACCTCATATTTTCG 670       680       690       700       710       720
CCCCTTGGCATATATAAGGCACACCAGTGTGGCAAGCCGTCTCTCAGATTGCATTTGCTG
GGGGAACCGTATATATTCCGTGTGGTCACACCGTTCGGCAGAGAGTCTAACGTAAACGAC 730       740       750       760       770       780
TCACGGATCTGTTTAGAACTGAAAGAAAAGGGGAAAGGGAGAGGGGGGAAAAAAGGGCAA
AGTGCCTAGACAAATCTTGACTTTCTTTTCCCCTTTCCCTCTCCCCCCTTTTTTCCCGTT

790
AAAGCTGCAGTGACTGTAA
TTTCGACGTCACTGACATT
```

GROWTH DIFFERENTIATION FACTOR PROMOTER AND USES THEREFOR

RELATED APPLICATIONS

This application claims priority to U.S. provisional Application No. 60/092,865, filed on Jul. 15, 1998, and U.S. provisional Application No. 60/123,270, filed on Mar. 8, 1999, incorporated herein in their entirety by this reference.

FIELD OF THE INVENTION

The invention relates to GDF promoters, such as GDF-8 promoters, as well as methods of using them, e.g., methods for screening for regulatory compounds of GDF-8 expression.

BACKGROUND OF THE INVENTION

GDF-8 is a member of the TGF-β superfamily, which encompasses a large group of growth and differentiation factors that play important roles in regulating embryonic development and in maintaining tissue homeostasis in adult mammals. GDF-8 appears to function specifically as a negative regulator of skeletal muscle growth and, therefore, has potential applications in producing livestock and game animals, such as cows, sheep, pigs, chicken, turkey, and fish which are relatively high in musculature and protein, and low in fat content. In addition, GDF-8 has potential applications in various cell proliferative and differentiation disorders, especially those involving muscle, nerve and adipose tissues in both human and animals. GDF-8 also appears to be involved in glucose transport and, therefore, has potential applications in the treatment or diagnosis of glucose transport associated disorders such as diabetes.

Many drug and diet regimens exist which may help increase muscle and protein content and lower undesirably high fat and/or cholesterol levels, but such treatment is generally administered after the fact, and is begun only after significant damage has occurred to the vasculature. Accordingly, it would be desirable to produce animals which are genetically predisposed to having higher muscle content, without any ancillary increase in fat levels. U.S. patent application Ser. No. 09/019,070, inventors Se-Jin Lee and Alexandra C. McPherron, filed Feb. 5, 1998 and entitled Growth Differentiation Factor-8 also describes the production of GDF-8, as well as potential uses. This application is also hereby incorporated by reference.

Control of GDF-8 gene expression is highly desirable. The availability of discreet DNA segments which are capable of conferring either a negative or positive control capability to known genes in eukaryotic systems is generally lacking in the art. Isolation of regulatory genetic sequences for GDF-8 is disclosed in the present invention.

SUMMARY OF THE INVENTION

The present invention relates to the molecular regulation of GDF-8 expression and, in particular, to the isolation and identification of regulatory sequences of GDF gene promoters, such as the GDF-8 gene promoter.

In one embodiment, the present invention provides the complete nucleotide sequence and identification of genetic regulatory elements which promote expression of GDF-8.

In another embodiment, the present invention provides a method of screening for compounds which regulate GDF-8 expression, for example, by inhibiting or by stimulating GDF-8 expression.

In yet another embodiment, the present invention provides a DNA expression construct containing the GDF-8 promoter operatively linked to a gene of interest (GOI), and a method of expressing a GOI in muscle and other tissues (e.g., tissues in which GDF-8 is naturally expressed).

BRIEF DESCRIPTION OF THE DRAWINGS

FIG. 7A shows the nucleotide sequence for the mouse GDF-8 promoter region (SEQ ID NO:4). FIG. 7B shows the nucleotide sequence for the chicken GDF-8 promoter region (SEQ ID NO:5).

FIG. 8 shows an alignment of the nucleotide sequences for human, mouse, pig and chicken GDF-8 promoter elements (SEQ ID NOS:6, 7, 8 and 9, respectively) upstream of the TATAA box (underlined). The CAAATG, CAGACA and GACAGC sequences are boxed. The shaded areas represent regions of sequence homology.

DETAILED DESCRIPTION OF THE INVENTION

Figures 1, 1A:
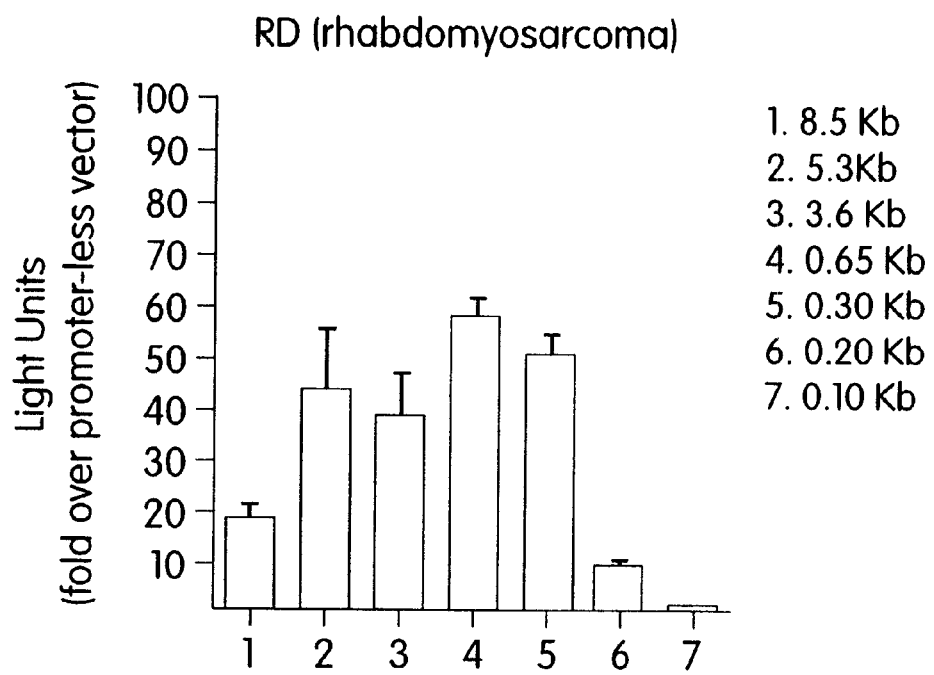
FIGS. 1A and 1B show the results of a human GDF-8 promoter-luciferase reporter construct transfection assay in 6 different cell lines.

The term a "GDF promoter," as used herein, refers to nucleotide sequence elements located upstream of the 5' end of a GDF gene (e.g., a gene encoding GDF-8 or another related or another homologous growth factor) which regulate (e.g., initiate, upregulate or downregulate) transcription and/or expression of the gene. For example, a GDF promoter can include sequence elements necessary to initiate gene transcription, enhancer elements, repressor elements and other cis-acting control elements which modulate gene expression. Accordingly, the term "GDF promoter" is used herein interchangeably with the term "GDF regulatory region" or "GDF control region."

An "isolated GDF promoter" refers to a GDF promoter which is removed from its natural sequence context. For example, an isolated GDF promoter can be a GDF promoter cloned or otherwise removed from its natural source, and inserted upstream from the 5' end of a heterologous structural gene, e.g., within an expression vector. The term "GDF promoter" also refers to nucleotide sequences having sufficient homology to a GDF promoter that it exhibits one or more functions of the GDF promoter (e.g., drives transcription of a gene operably linked to the promoter). Generally, GDF promoters are derived from the 5' flanking region of a GDF gene.

GDF promoters of the invention include those derived from any GDF gene, such as the GDF-8 gene or a homologous gene (e.g., GDF-11). The term "derived from", as it is used herein, refers to a source or origin for an isolated GDF promoter of the invention. For example, a GDF promoter that is "derived from" a particular GDF gene (e.g., a GDF-8 gene) will be identical or highly homologous in nucleotide sequence to the GDF promoter of a naturally occurring GDF gene (e.g., a GDF-8 gene). Isolated GDF promoters of the invention which are "derived from" GDF genes, such as GDF-8 genes, also include those which have been modified by insertion, deletion or substitution of one or more nucleotides but which retain substantially the same activity or function.

Figure 8:
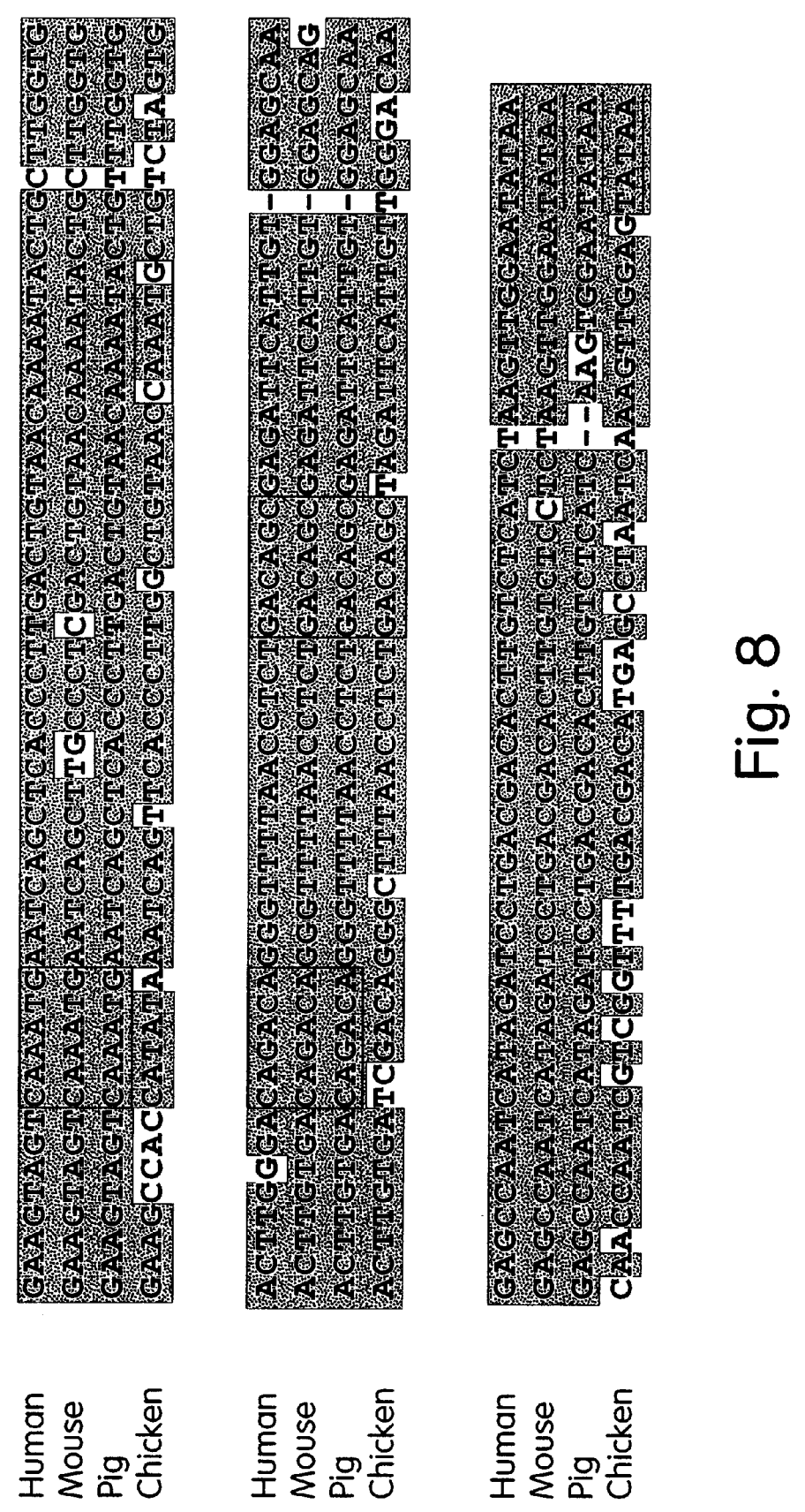

The term "a GDF gene" refers to a GDF gene from any naturally possessing the GDF gene, including, but not limited to human, chicken, cow, sheep, fish, pig and mouse. A "GDF gene" also refers to a GDF gene from any piscine, crustacean or mollusk naturally possessing the GDF gene. In a specific embodiment, the invention provides a human GDF-8 promoter comprising all or a portion (or portions) of the nucleotide sequence shown in FIG. 2 (SEQ ID NO:1), as well as GDF-8 promoters from other mammals having regions of homology to the human promoter sequence, particularly in regions required for activity of the promoter sequence. Generally, this range of homology is about 60% to 90% or higher. For example, homologous regions within GDF-8 promoters from human (SEQ ID NO:6), mouse (SEQ ID NO:7), pig (SEQ ID NO:8) and chicken (SEQ ID NO:9) GDF-8 genes are shown in FIG. 8.

Accordingly, GDF promoters of the invention include promoters having a nucleotide sequence at least 60%, 65%, 70%, 75%, 80%, 85%, 90%, 95%, 98%, or more identical to the nucleotide sequence set forth in SEQ ID Nos:1, 4, 5, 6, 7, 8 and 9, and which modulate expression of a gene operably linked to the promoter. To determine the percent identity of two nucleic acid sequences, the sequences are aligned for optimal comparison purposes (e.g., gaps can be introduced in one or both of a first and a second nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The nucleotides at corresponding nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

Accordingly, GDF promoters of the invention can be identified by comparing the regions 5' of the transcription initiation site of GDF genes to the specific GDF promoter sequences provided herein (e.g., SEQ ID NO:1 corresponding to the human GDF-8 promoter) and looking for regions of homology, corresponding to the active promoter sequences. The specific GDF-8 promoter sequences provided by the present invention also can be used to screen for homologous sequences from other species using standard DNA hybridization protocols (e.g., under conditions of high stringency).

GDF promoters of the invention contain DNA sequence elements which ensure proper binding and activation of RNA polymerase, influence where transcription will start, and affect the level of transcription. In addition, specific regulatory sequences that are functional in the regulation (induction and repression) of gene expression responsive to stimuli or specific chemical species also may be included within the promoter sequence.

A DNA "coding sequence", "coding region", or a "sequence encoding" a particular protein is a DNA sequence which is transcribed and translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, cDNA from eukaryotic mRNA, genomic DNA sequences from eukaryotic (e.g., mammalian, animal, avian etc.) sources, and even synthetic DNA sequences. A transcription termination sequence will usually be located 3' to the coding sequence.

The term "reporter gene", as used herein, refers to a gene encoding a protein which is readily quantifiable or observable. Because gene regulation usually occurs at the level of transcription, transcriptional regulation and promoter activity are often assayed by quantitation of gene products. For example, promoter regulation and activity has often been quantitatively studied by the fusion of the easily assayable *E. coli* lacZ gene to heterologous promoters (Casadaban and Cohen (1980) J. Mol. Biol. 138:179–207). The structural gene for chloramphenicol acetyl transferase (CAT), green fluorescence protein (GFP), and luciferase are other genes commonly used to detect activity of a promoter or other regulatory sequence.

The term "tissue-specific expression", as it is used herein, refers to a limited or characteristic pattern of gene expression among cell types. In other words, expression of a gene is observed in certain tissues of an organism but not in other tissues. For example, "muscle-specific" expression of a gene denotes that that gene is expressed in the muscle and perhaps limited other tissues, but is not expressed in all tissues (e.g., globally).

A "vector" is a replicon, such as a plasmid, phage, or cosmid, to which another DNA segment may be attached so as to bring about the replication of the attached segment. An "expression vector" means any DNA vector (e.g., a plasmid vector) containing the necessary genetic elements for expression of a desired gene, including a promoter region of the present invention. These elements are "operably linked" to the gene, meaning that they are located at a position within the vector which enables them to have a functional effect on transcription of the gene. The regulatory elements need not be contiguous with the coding sequence, so long as they function to direct the expression thereof. Thus, for example, intervening untranslated yet transcribed sequences can be present between a promoter and the coding sequence and the promoter can still be considered "operably linked" or "in operable linkage to" the coding sequence.

A cell has been "transformed" by exogenous DNA (e.g., a transgene) when such exogenous DNA has been introduced inside the cell membrane. Exogenous DNA may or may not be integrated into the chromosomal DNA comprising the genome of the cell. With respect to eukaryotic cells, though, a stably transformed cell is one in which the exogenous DNA has become integrated into the chromosome such that it is inherited by daughter cells though chromosome replication.

A "host cell" is a cell that has been transformed, or is capable of transformation, by an exogenous nucleic acid molecule.

A "transgene" refers to a nucleic acid which is introduced into a cell. Typically, the transgene is integrated into the genome of the cell following introduction. The transgene can encode a protein which is not expressed in the cell or which is expressed in the cell at low levels or in defective form.

A "transgenic animal" is an animal carrying in its cells at least one transgene. For example, the transgenic animal can contain in its cells a transgene corresponding to a gene of another species which has been introduced into the germline of the animal, such that the introduced gene is present in all somatic and germline cells.

GDF promoters of the invention can vary in size. Generally, the promoter sequence spans or is located within approximately 500 bases to 3000 bases of sequence in the 5' direction (or upstream) to the site of transcription initiation. However, the promoter can include sequences out to approximately 4000 bp or further 5' to the site of transcription initiation. When employed in the context of a heterologous structural gene, the optimal location of the GDF promoter with respect to the transcription initiation site can vary. Generally, the same benefit will be obtained when the GDF promoter is located anywhere up to about 300 nucleotides or more upstream from the transcription initiation site. However, in a preferred embodiment, the GDF promoter is located within 150 nucleotides of the transcription initiation site.

The majority of promoters control initiation of transcription in one direction only. Therefore, in order to be under the control of a GDF promoter of the invention, a structural gene generally must be located downstream (in the 3' direction) of the GDF promoter and in the correct orientation with respect to the promoter. One or several genes may be under the control of a single GDF promoter or, conversely, one or more GDF promoters may control a single structural gene.

In one embodiment, the GDF promoter regulates expression of a gene operatively linked to the promoter by changing the ability of RNA polymerase to bind to DNA sequences within the GDF promoter. For example, a regulatory protein can bind to a DNA sequence at or near the position of RNA polymerase binding to enhance or prevent transcription. Alternatively, a regulatory protein (e.g., an inducer or repressor molecule) can directly or indirectly interact with RNA polymerase itself to change its specificity for recognition and binding to a DNA sequence of the GDF promoter. In either case, specific sequence(s) within the GDF promoter are involved in the mechanism of regulation.

The term "recombinant DNA molecule" is used herein to distinguish DNA molecules in which heterologous DNA sequences have been artificially cleaved from their natural source or ligated together by the techniques of genetic engineering, for example, by in vitro use of restriction enzymes or ligation using DNA ligase.

GDF promoters of the invention can be identified and cloned from their natural sources (e.g., the genome of a human, mouse, chicken, pig, cow, fish or sheep). The process of cloning a DNA fragment involves excision and isolation of the DNA fragment from its natural source, insertion of the DNA fragment into a recombinant vector and incorporation of the vector into a microorganism or cell where the vector and inserted DNA fragment are replicated during proliferation of the microorganism or cell. The term "cloned DNA fragment" or "cloned DNA molecule" refers to a DNA fragment or molecule produced by the process of cloning, as well as copies (or clones) of the DNA fragment or molecule replicated therefrom. Standard techniques for cloning, DNA isolation, DNA amplification and purification, enzymatic reactions (e.g., involving DNA ligase, polymerase, or restriction endonucleases) and various separation techniques, which known and commonly employed by those skilled in the art, can be used in the present invention. A number of these standard techniques are described in: Maniatis et al. (1982) Molecular Cloning, Cold Spring Harbor Laboratory, Cold Spring Harbor, N.Y.; Wu (ed.)(1979) Meth. Enzymol 68; Wu et al. (Eds.) (1983) Meth. Enzymol. 100 & 101; Grossman and Moldave (eds.) (1980) Meth. Enzymol. 65; Miller (ed) (1972) Exp. Mol. Genetics, Cold Spring Harbor, N.Y.; Old and Primrose (1981) Principles of Gene Manipulation, Univ. of Cal. Press, Berkely; Schlief and Wensink (1982) Practical Methods in Molecular Biology; Glover (ed) 1985(DNA Cloning, Vols. I and II, IRL Press, Oxford, UK; Sellow and Hollaender (1979) Genetic Engineering: Principles and Methods, Vols I, Plenum Press, N.Y.; which are incorporated by reference in their entirety herein. Abbreviations, where employed, are those deemed standard in the field and commonly used in professional journals such as those cited herein.

Expression of a gene requires both transcription of DNA into mRNA and the subsequent translation of the mRNA into a protein. Because gene regulation usually occurs at the level of transcription, transcriptional regulation and activity of GDF promoters of the present invention can be assayed by quantitation of gene products. For example, promoter regulation and activity can be quantitatively studied by the fusion of the easily assayable E. Coli lacZ gene sequence to a heterologous promoter (Casadaban and Cohen (1980) J.

Mol. Biol. 138:179–207). Alternatively, the genes coding for chloramphenicol acetyl transferase (CAT), green fluorescence protein (GFP) and luciferase can be used to detect activity of a promoter. Such genes are termed "reporter" genes which, when combined with a given promoter (usually a heterologous promoter), provide a ready assay for promoter activity.

GDF promoters and GDF promoter elements of the invention (i.e., selected sequences within GDF-8 promoters involved in their regulatory function) may be employed in the form of single or multiple units, in numerous various combinations and organizations, in forward or reverse orientations, and the like. In the context of multiple unit embodiments and/or in embodiments which incorporate both positive and negative control elements, there is no requirement that such units be arranged in an adjacent head-to-head or head-to-tail construction since the improved regulation capability of such multiple units is conferred virtually independent of the location of such multiple sequences with respect to each other. Moreover, there is not requirement that each unit comprise the same positive or negative element. Such sequences can be located upstream of and sufficiently proximal to a transcription initiation site, in the intron or downstream of the gene of interest, to confer a desired regulatory effect. In addition, GDF promoter and GDF promoter elements of the invention can be used in numerous various combinations with promoters and regulatory elements of other genes to achieve the desired enhancement or repression of the expression of any gene of interest.

Accordingly, in one embodiment of the invention, the GDF promoter is used to regulate transcription of a heterologous structural gene by simply obtaining the structural gene and inserting one or more copies of the GDF promoter upstream of the gene's transcription initiation site. Additionally, as is known in the art, it is generally desirable to include TATA-box sequences upstream of and proximal to the transcription initiation site of the heterologous structural gene. Such sequences may be synthesized and inserted in the same manner as the novel control sequences of the invention. Alternatively, the TATA sequences naturally associated with the heterologous structural gene can be employed. Generally, the TATA sequences are located between about 20 and 30 nucleotides upstream of transcription initiation.

Numerous methods are known in the art for precisely inserting selected nucleotide sequences, at selected points, within larger sequences. In one method, the desired control sequences, or combinations of sequences, are synthesized and restriction site linker fragments added to the control sequence termini. This allows for ready insertion of the control sequences into compatible restriction sites within upstream regions. Alternatively, synthesized control sequences can be ligated directly to selected regions. In addition, site specific mutagenesis can be employed to fashion restriction sites into which control sequences may be inserted, in the case where no convenient restriction sizes are found at a desired insertion site.

GDF promoters of the present invention can be beneficially employed in the context of any heterologous gene, with or without additional homologous or heterologous control or promotion sequences. In a particular embodiment, the present invention provides the GDF-8 gene promoter and optionally other regulatory sequences which function in the induction of GDF-8 expression in response to factors which are known to induce GDF-8 expression.

Any suitable reporter gene can be used to measure the activity of a GDF promoter element of the invention. For example, in the examples described below, a GDF-8 promoter-luciferase reporter construct was used. The GDF-8 promoter-luciferase reporter construct was active in two cell lines (FIGS. 1A–1B), RD (human embryonal rhabdomyosarcoma) and A673 (human rhabdomyosarcoma). Maximum activity was observed with the 0.65 Kb 5' flanking fragment (5–8% of the SV40 luciferase reporter plasmid, pGL3-control). No significant luciferase activities were detected in the HepG2 (human liver hepatoblastoma), HT29 (human colon adenocarcinoma), PA-1 (human ovarian teratorcarcinoma), and MCP-7 (human breast adenocarcinoma). The results of the transfection assays suggest that 1) a repressor element(s) exists between 8.5 Kb and 0.65 Kb upstream of the human GDF-8 gene, 2) the 0.65 Kb fragment contains the minimal promoter, and 3) the minimal promoter is tissue specific and appears to be active in muscle cell lines only.

In yet another embodiment, the present invention provides a method of screening for a compound which binds to a GDF promoter (or a portion thereof), such as a GDF-8 promoter), and modulates expression of a GDF gene (e.g., GDF-8) or a heterologous gene. As used herein, the term "modulate" includes both inhibition and stimulation of GDF expression. Moreover, the term "inhibition" is intended to include both complete and partial inhibition of GDF expression. In various embodiments, GDF expression is inhibited to a level at least 1.2-fold, 1.5-fold, 1.8-fold, 2-fold, 2.5-fold, 3-fold, 4-fold or 5-fold lower than the wild type level of GDF-8 expression. In further embodiments, GDF expression is inhibited by at least 10%, 20%, 30%, 40%, 50%, 75% or 100%.

To test compounds for their ability to modulate GDF transcription and/or expression, the compound can be tested for its ability to increase or stimulate the transcription and/or expression or to decrease or inhibit the transcription and/or expression of a reporter gene (e.g., the SV40 β-galactosidase reporter gene) which is operatively linked to a GDF promoter of the invention, compared to that of a control reporter. Effects of the test compound are determined by changes in reporter gene activity. For example, a stable cell line containing a GDF-8 promoter operatively linked to a reporter gene, such as the luciferase gene, can be used in any well-known screening method known in the art for detecting expression (e.g., luciferase assays, CAT assays, or Green Fluorescent Protein (GFP) assays). However, the invention is not restricted to these suggested screening methods.

Transcription factors that bind to GDF promoters of the invention also can be characterized using gel mobility shift assays and these transcription factors can be cloned using these specific sequences as probes in screening expression libraries. Alternatively, second generation reporter constructs containing multiple copies of the following transcription factor binding sequences: CAAATG, CAGACA or GACAGC and a minimal promoter (0.2 kb upstream of initiating ATG), or a combination of these sequences and a minimal promoter, can be used in high-throughput screening assays to identify inhibitors specific for GDF genes which operate by binding to GDF promoter sequences. After these transcription factors have been identified, they too, may be used as targets for identifying other inhibitors. For example, these transcription factors can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), or as protein probes in the screening of expression libraries to identify other proteins, which bind to or interact with the transcription factors. Such transcription factor-binding proteins are also likely to act as modulators, e.g., inhibitors of GDF-8 expression.

In one embodiment, the invention provides a GDF-8 promoter, or a portion thereof, which can be operatively linked to a gene of interest (GOI) and expressed in a tissue-specific manner. GDF-8 promoter activity is specific to muscle tissue. Therefore, the GDF-8 promoter can be used to express any GOI for which expression is desired in muscle tissue. Examples of such genes include, but are not limited to, GDF-8 itself, dystrophin, growth factors, genes coding for tumor or pathogens antigens. Genes which express proteins useful in vaccination are also encompassed, including viral, tumor, pathogenic, or bacterial antigens, specifically AIDS envelope protein gp120. However, this is not intended to be a limiting list. Any gene which expresses a protein of interest may be employed in the methods of the invention.

Expressing a protein of interest specifically in muscle tissue is highly preferred in the area of gene therapy due to the amount of muscle mass in the body and the ease in which muscle can express foreign genes. Accordingly, the GDF-8 promoter of the invention can be used in gene therapy vectors to direct expression of a gene of interest in muscle tissue. Gene therapy vectors including the GDF-8 promoter of the invention can be delivered to a subject by, for example, intravenous injection, local administration (see U.S. Pat. No. 5,328,470), stereotactic injection (see e.g., Chen et al. (1994) *Proc. Natl. Acad. Sci. USA* 91:3054–3057), or direct intramuscular injection (as described in, for example, U.S. Pat. Nos. 5,580,859 and 5,589,466). The gene therapy vectors containing the GDF-8 promoter of the invention can be used for the treatment of a muscle-associated disorder such as cancer, muscular dystrophy, spinal cord injury, traumatic injury, congestive obstructive pulmonary disease, AIDS or cachexia; or for the treatment of obesity and related disorders, e.g., diabetes; or disorders related to abnormal proliferation of adipocytes.

This invention is further illustrated by the following examples which should not be construed as limiting. The contents of all references, patents and published patent applications cited throughout this application are incorporated herein by reference.

EXAMPLES

Example 1
Screening of Human Genomic Library

A Stratagene human genomic library (HT1080) was screened using a 745 bp EcoRI-Hind III human GDF-8 cDNA probe (described in, for example, U.S. patent application Ser. No. 08/525,596). Three genomic clones were isolated using methods described in Current Protocol in Molecular Biology, Eds. Ausubel et al., John Wiley & Sons, Inc., 996). An 8.5 kilobase (Kb) fragment containing the 5' flanking region of human GDF-8 was subcloned into the luciferase reporter construct pGL-3-basic (Promega). This 8.5 kilobase fragment was truncated by a restriction digestion or by PCR to generate six additional clones: 5.3 Kb, 3.6 Kb, 0.65 Kb, 0.3 Kb, 0.2 Kb, and 0.1 Kb. Approximately 1 Kb upstream, of the initiating ATG has been sequenced. The approximate transcription start site, based on the positions of the CCAAT and TATAA boxes is about 100 bases upstream of the ATG. Therefore, the luciferase clone containing 0.1 Kb contains only the 5' untranslated region.

Example 2
Transfection Assays

Transient transfection assays were performed using FuGENE (Boehringer Mannheim) according to the manufacturer's protocol. Six different human cell lines, RD, A673, HepG2, HT29, PA-1, and MCF-7 (ATCC, Rockville, Md.) were used in the transfection assays. On the day before transfection, $1.5 \times 10^5$ cells in 2 ml of DMEM with 10% FBS were seeded in 35 mm tissue culture dishes. The cells were incubated overnight until the cells were 50–70% confluent. For each transfection, 1.0 μg of luciferase reporter plasmid, 0.1 μg of β-galactosidase reporter plasmid, pSV-β-gal (Promega), and 5 μg of FuGENE was used. A promoter-less luciferase vector (pGL3-basic)(Promega) and a SV40 luciferase vector (pGL3-control)(Promega) were used as controls. Luciferase and β-galactosidase activities were determined 24 hours post-transfection using the Dual Light chemiluminescent reporter gene assay kit (Tropix, Inc.) according to the manufacturer's protocol. The relative activities of the luciferase reporter constructs were normalized to the β-galactosidase activity.

Example 3
GDF-8 Promoter Mutants

Figures 1, 1A, 2:
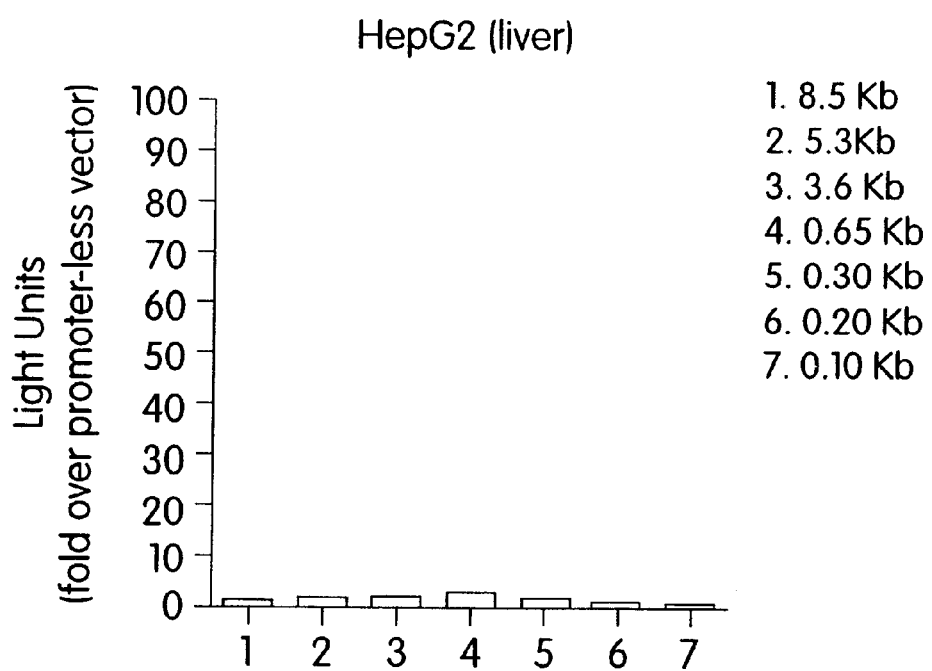
FIG. 2 shows the nucleotide sequence corresponding to the human GDF-8 promoter element (SEQ ID NO:1). The initiation codon, ATG, is underlined in bold letters. The boxed sequences are the three mutated regions. The numbers represent the nucleic acid positions upstream of the ATG.
Figures 1, 1A, 2, 3:
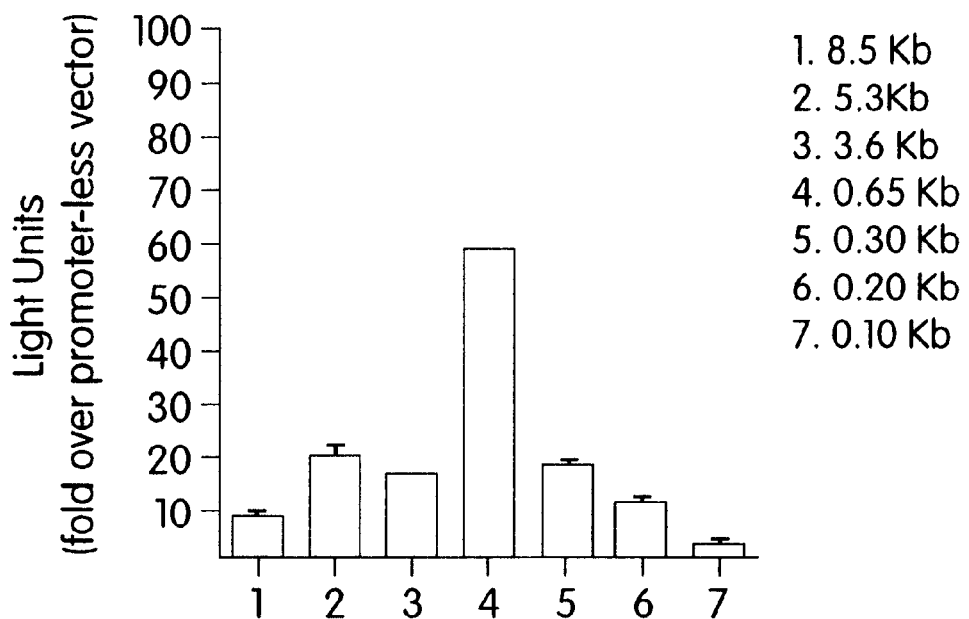
Figures 1, 1A, 2, 3, 4:
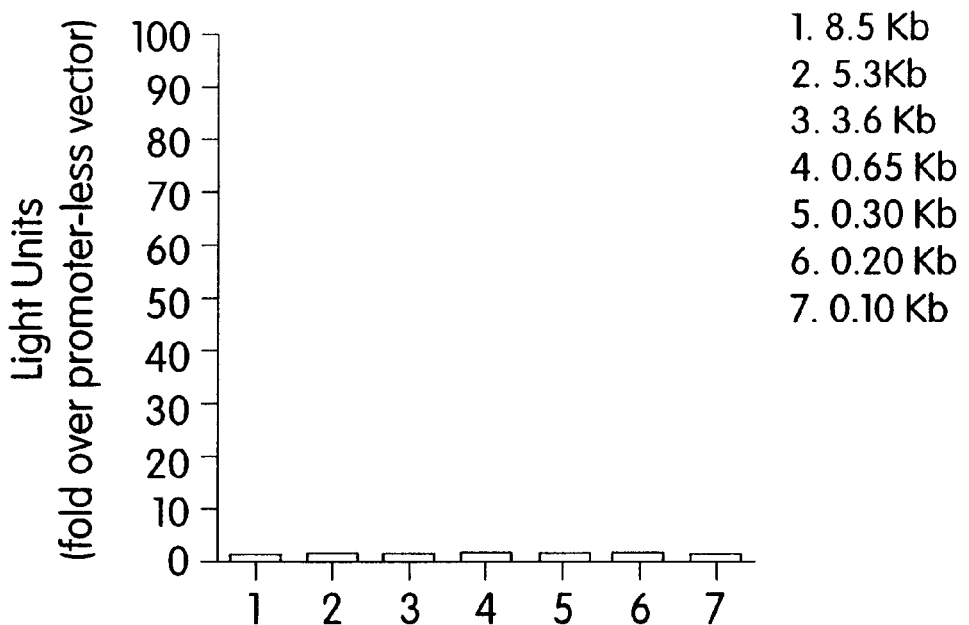
Figures 1, 1B:
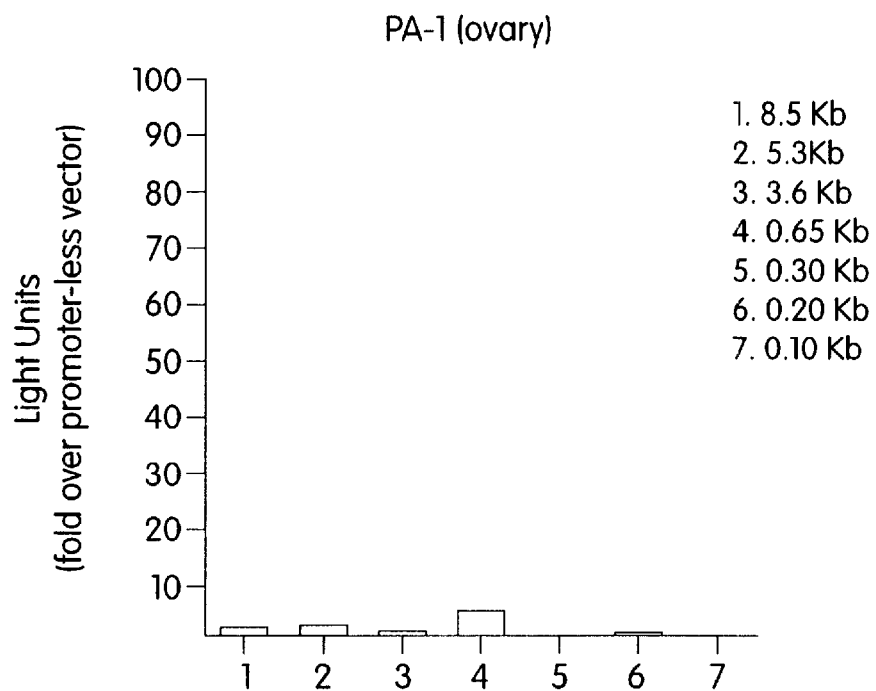
Figures 1, 1B, 2:
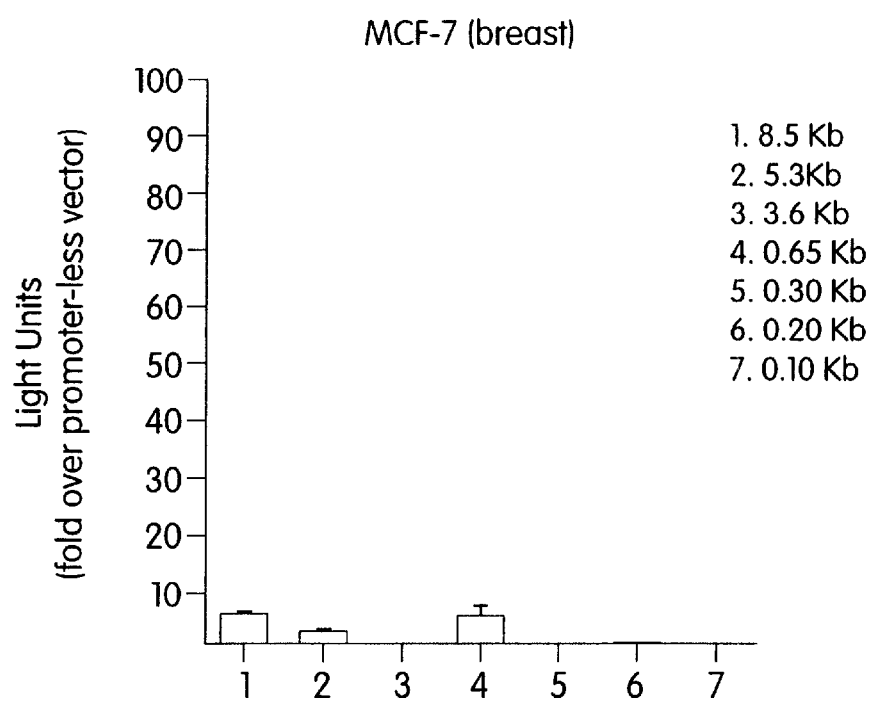
Figure 3A:
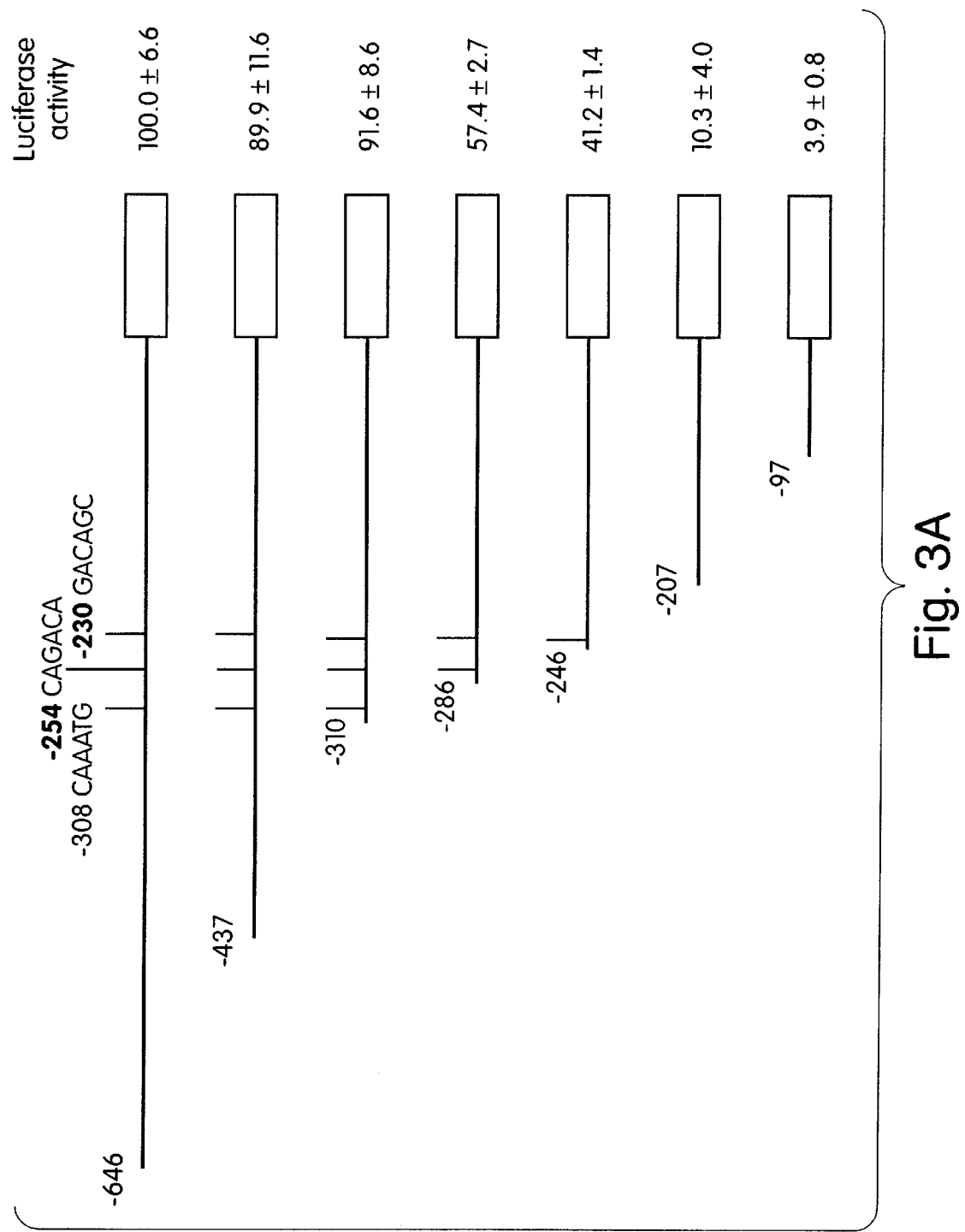
FIG. 3A is a schematic representation of various human GDF-8 promoter reporter constructs.
Figure 3B:
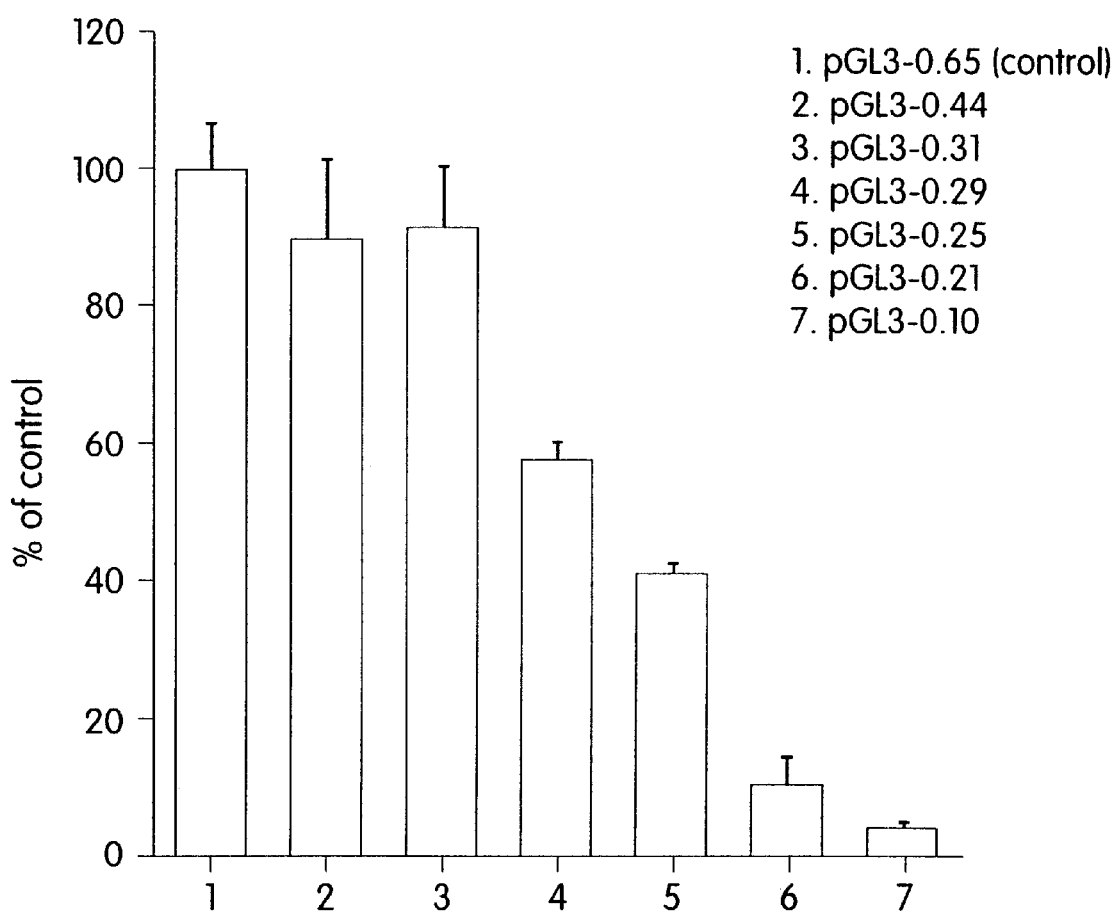
FIG. 3B is a graph showing the Luciferase activity of these constructs in RD (human embryonal rhabdomyosarcoma) cells. Luciferase activities are expressed as percent of control (pGL3-0.65, luciferase reporter plasmid containing 0.65 Kb of sequence upstream of the ATG site). The relative luciferase activities of the reporter plasmids are normalized to the β-galactosidase activity.

Additional truncations of the GDF-8 promoter were made using PCR to generate DNA fragments containing 0.65 Kb, 0.44 Kb, 0.31 Kb, 0.29 Kb, 0.25 Kb, 0.21 Kb, and 0.1 Kb of sequence upstream of the initiating ATG codon (see FIGS. 2 and 3A). These DNA fragments were then subcloned into the luciferase reporter plasmid, pGL3-basic (Promega). The constructs (0.65 Kb to 0.1 Kb) were transfected into RD cells and the expression of these constructs was determined using luciferase assays (see FIGS. 3A and 3B). Deleting the region from 0.31 Kb to 0.29 Kb decreased the luciferase activity by about 40%; from 0.31 Kb to 0.25 Kb decreased the luciferase activity by about 60%; and from 0.31 Kb to 0.21 Kb decreased the luciferase activity by about 90%. Examination of the regions from 0.31 Kb to 0.29 Kb, and 0.29 Kb to 0.25 Kb, revealed the sequence CAAATG (potential E-box) and CAGACA (potential Smad 3 and 4 binding sequence), respectively. Although examination of the 0.25 Kb to 0.21 Kb region did not reveal any known transcription binding sites, the deletion results suggest the possibility of a cis-element.

Figure 4A:
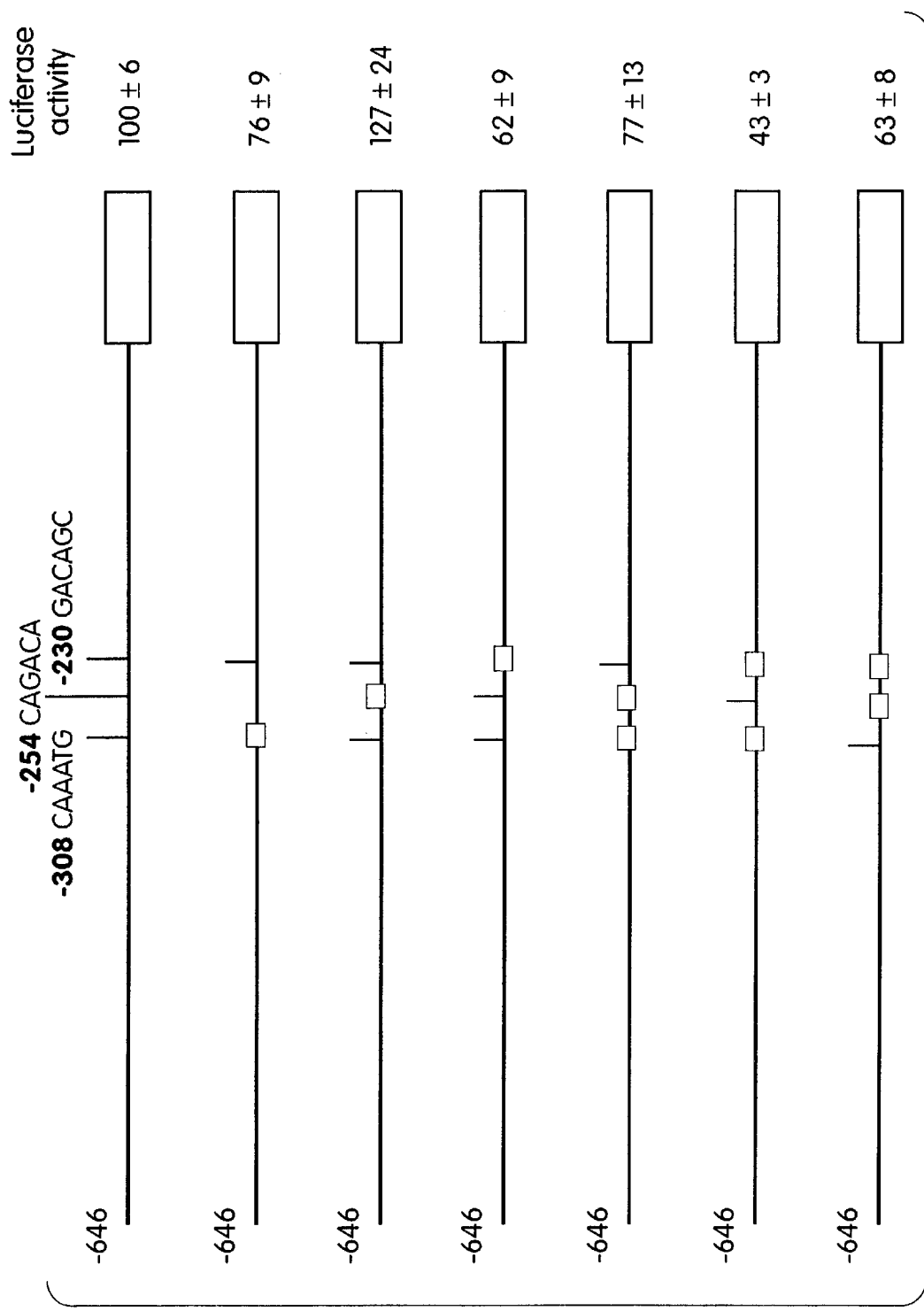
FIG. 4A is a schematic representation of various mutated human GDF-8 promoter-luciferase reporter constructs.
Figure 4B:
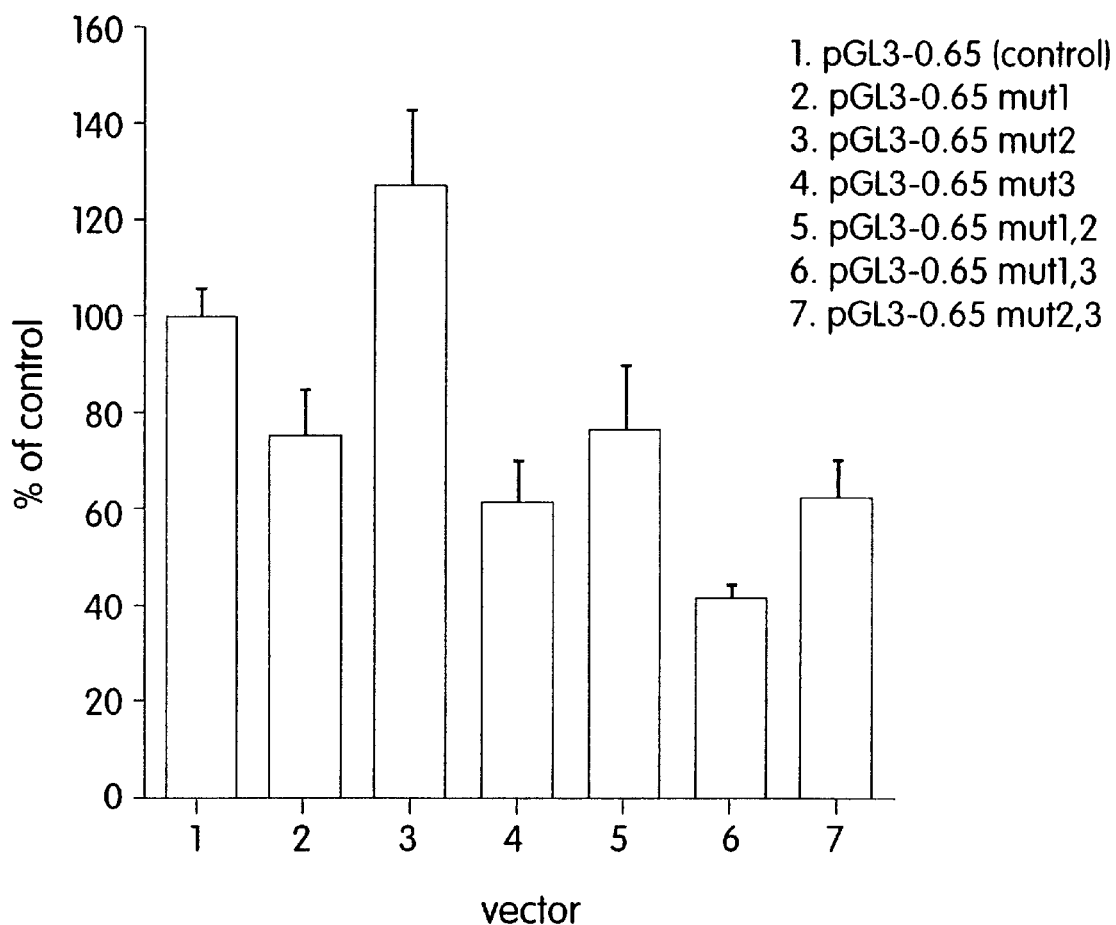
FIG. 4B is a graph showing the luciferase activity of these constructs in RD cells. Luciferase activities are expressed as percent of control (pGL3-0.65, luciferase reporter plasmid containing 0.65 Kb of sequence upstream of the ATG site). The relative luciferase activities of the reporter plasmids are normalized to the β-galactosidase activity.

To determine whether the decrease in luciferase activity from the deletion constructs was due to the regulatory role of the CAAATG, CAGACA and GACAGC sequences in GDF-8 expression, or due to the physical truncation of the promoter region, clustered site-directed mutagenesis, using the QuikChange™ site-directed mutagenesis kit (Stratagene), was performed. The following mutants were created (CAAATG→AGATCT; CAGACA→AGATCT; and GACAGC→AGATCT). In addition, GDF-8 promoter reporter constructs containing multiple clustered mutations were also generated. The mutated promoter constructs were transfected into RD cells and assayed for luciferase activity (see FIGS. 4A and 4B). Mutating the CAAATG region resulted in approximately 25% decrease in luciferase activity; mutating the CAGACA region resulted in an increase in luciferase activity; and mutating the GACAGC region resulted in approximately 40% decrease in luciferase activity.

These results suggest that not only does the physical truncation of the promoter region have an effect on luciferase expression, but more importantly, that the sequences CAAATG, CAGACA and GACAGC play a regulatory role in expression. The two sequences, CAAATG and GACAGC, also appear to act synergistically as demonstrated by a 60% decrease in luciferase activity in the double mutant. These results also suggest that there are multiple regulatory regions (e.g., transcription factor binding regions) in the GDF-9 promoter. Therefore, GDF-8 promoter-luciferase gene reporter constructs can be used in high-throughput screenings (HTS) for inhibitors of GDF-8 expression may yield inhibitors acting at different regulatory sites.

Figure 5A:
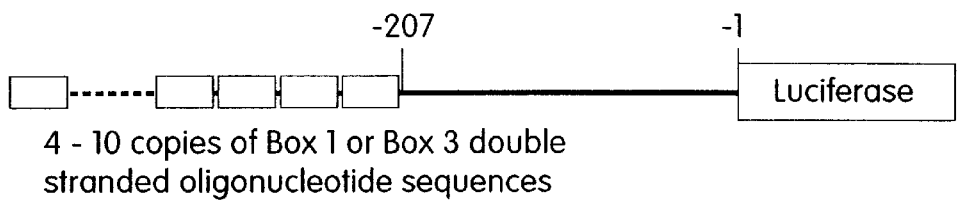
FIG. 5A shows the double stranded DNA oligonucleotide sequences used in constructing human GDF-8 promoter-luciferase reporter constructs containing concatemers of CAAATG and GACAGC sequences. Box 1 sequence corresponds to SEQ ID NO:2. Box 3 sequence corresponds to SEQ ID NO:3.
Figure 5B:
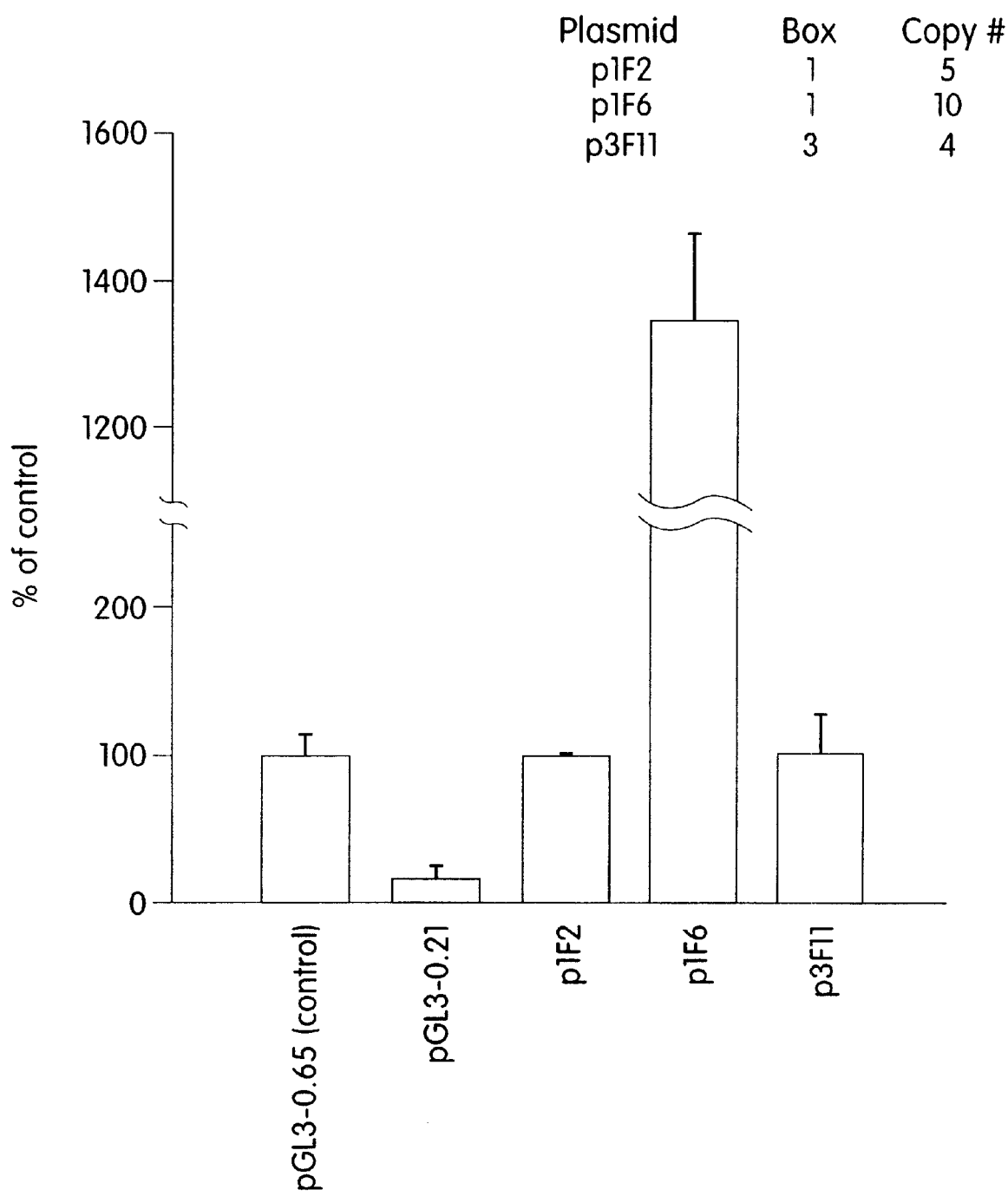
FIG. 5B is a graph showing the luciferase activity of these constructs in RD cells. Luciferase activities are expressed as percent of control (pGL3-0.65, luciferase reporter plasmid containing 0.65 Kb of sequence upstream of the ATG site). The reporter construct pGL-0.21 is the parental plasmid of the concatemer reporter constructs. The relative luciferase activities of the reporter plasmids were normalized to the β-galactosidase activity.

Example 4
Generation of Expression Constructs Suitable for Use in Screening for Regulatory Compounds of GDF-8 Expression The mutation of the sequences CAAATG, CAGACA and GACAGC results in either inhibiting (for CAAATG and GACAGC) or enhancing (for CAGACA) the expression of the GDF-8 promoter construct pGL3-0.65. This indicates that these sequences are involved in the regulation of GDF-8 expression and suggests that these sequences are recognized by transcription factors. To demonstrate this, Luciferase expression plasmids containing a minimal promoter sequence (PGL3-0.21 containing. the region −1 to −207, FIG. 2) and one or more copies of the above regulatory sequences upstream of the minimal promoter sequence were constructed. FIG. 5A shows the double stranded oligonucleotide sequences containing the sequences CAAATG and GACAGC and their flanking sequences used in the generation of concatemers (multiple copies of the above-identified sequences). Expression of the luciferase reporter constructs containing the CAAATG sequence was dependent on the number of copies of this sequence contained within the construct, while the expression of the luciferase reporter constructs remains 100% of the control regardless of the number of copies of the GACAGC sequence (FIG. 5B). These transfection results indicate that these expression plasmids can be used in screening protocols to identify compounds that regulate specific transcription factors interacting with the above regulatory sequences.

The approaches described in this Example, as well as Examples 1, 2 and 3 above, can also be used to identify any other unknown regulatory sequences in the human GDF-8 promoter and other GDF-8 promoter, including but not limited to mouse, pig or chicken GDF-8 promoters. In addition, the various expression constructs described in this Example, as well as Examples 1, 2 and 3 above, can be used to generate transgenic animals to demonstrate promoter and/or regulatory activity in vivo.

Figure 6:
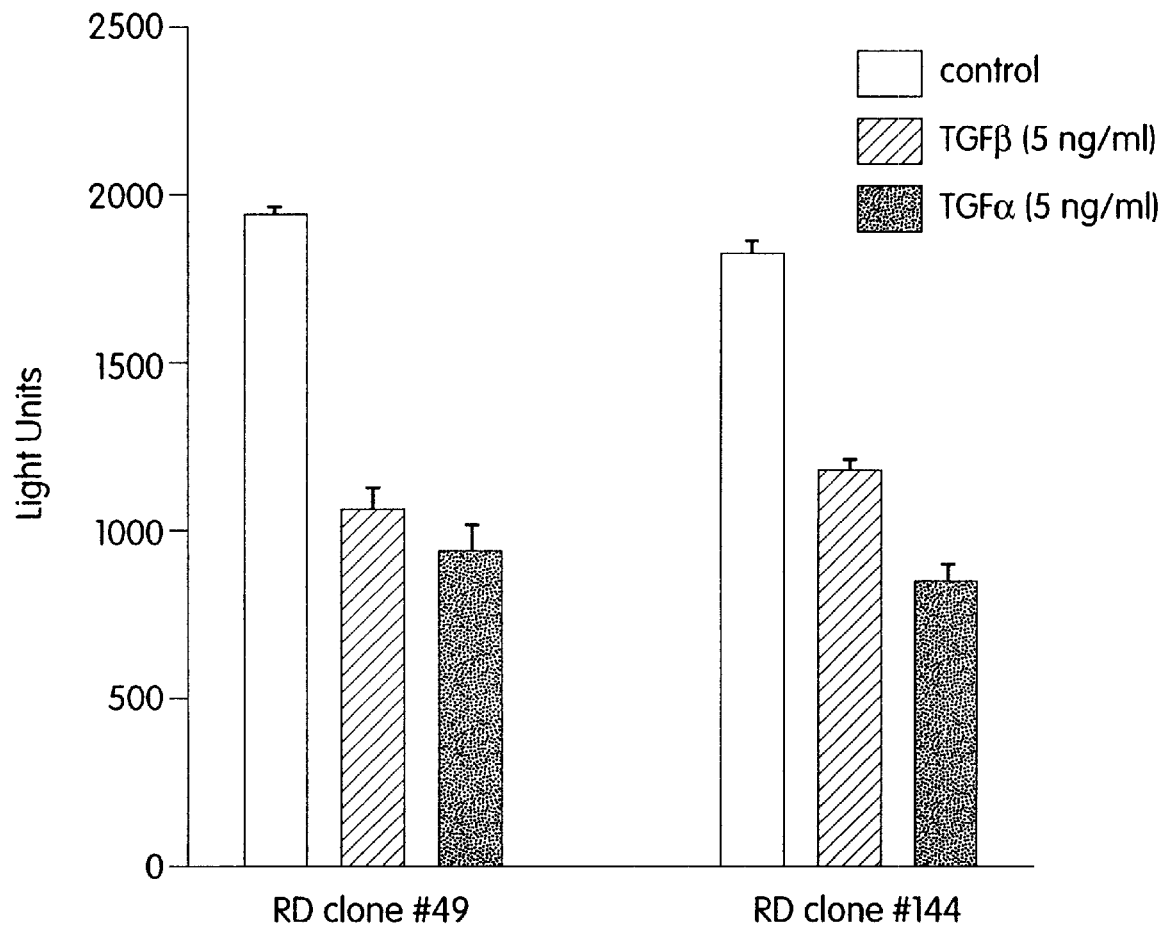
FIG. 6 is a graph showing the luciferase activities of the various stable RD clones containing the pGL3-0.65 luciferase reporter sequence referred to in the description of FIG. 5B, and the effects of TGF-β and TNFα on luciferase reporter expression.

Example 5
Generation of Cell Lines Suitable for Use in Screening for Regulatory Compounds of GDF-8 Expression Stable cell lines containing the pGL3-0.65 plasmid sequence were generated by transfecting RD cells with the pGL3-0.65 plasmid and selecting for stable cell clones under G418 pressure selection. The expression profiles of two such stable cell clones are shown in FIG. 6. Treatment of these cell clones with TGF-β or TNFα down regulated the luciferase reporter gene expression demonstrating that the exogenous GDF-8 promoter can be regulated and that these cell clones are useful in the screening and identification of GDF-8 expression regulatory compounds. Stable cell lines containing CAAATG and GACAGC concatemer reporter plasmids (described in Example 4) can also be generated for use in the screening and identification of GDF-8 expression regulatory compounds, e.g., compounds that specifically affect regulatory proteins (such as transcription factors) binding to these sequences.

Example 6
Regulatory Sequences in GDF-8 Promoters Are Conserved Among Various Species Additional promoter sequences from chicken and mouse GDF-8 were obtained by sequencing a chicken GDF-8 genomic clone, isolated by screening a White Leghorn Chicken genomic library (Stratagene), and by screening a mouse GDF-8 genomic clone, kindly provided by Dr. Se-jin Lee at Johns Hopkins University (see McPherron et al. (1997) Nature 387:83–90). The nucleotide sequence for the pig GDF-8 gene can be obtained from GenBank Accession numbers AJ133580 and AF093798.

A comparison of human, mouse, chicken and pig GDF-8 promoter sequences (160 nucleotides upstream of the TATAA box) is shown in FIG. 8 and reveals a high level of sequence homology between the four species (see Table 1). In particular, the regulatory sequences CAAATG and GACAGC are present within this region in all four species. The high degree of sequence identity in the promoter regions of these species and the conservation of these regulatory sequences in this region indicates that the same transcription factors that bind to the human promoter also can recognize regulatory sequences in pig, mouse and chicken. Therefore, the same strategies that can be used to identify regulatory sequences in the human promoter can also be used to identify regulatory sequences in the promoter regions of mouse, pig and chicken GDF-8.

The activity of the promoter and regulatory elements of the mouse, pig and chicken GDF-8 genes can be determined and analyzed using methods described for the human GDF-8 gene in Examples 1, 2, 3 and 4. For example, cells and cell lines of mouse, pig and chicken origin can be used in the in vivo analysis of mouse, pig and chicken GDF-8 promoter and regulatory elements, respectively. Since the GDF-8 promoter region is highly conserved among the different species, in addition to using cells and cell lines from homologous species in analyzing promoter and regulatory element activities in in vivo assays, cells and cell lines of heterologous species may also be used. Additionally, the GDF-8 promoter and regulatory element activities of any species including, but not limited to, human, mouse, pig and chicken, can be analyzed in vivo by the generation of transgenic animals using reporter vectors containing the GDF-8 promoter, portion of the promoter, regulatory elements and/or combinations thereof.

TABLE 1

| % Sequence Homology | Human | Pig | Mouse | Chicken |
|---|---|---|---|---|
| Human | 100 | 97 | 96 | 79 |
| Pig |  | 100 | 95 | 78 |
| Mouse |  |  | 100 | 76 |
| Chicken |  |  |  | 100 |

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated GDF gene promoter comprising the nucleotide sequence of SEQ ID NO:1.

2. The isolated GDF gene promoter of claim 1, wherein said GDF gene promoter is derived from a GDF-8 gene.

3. The isolated GDF gene promoter of claim 2, wherein the GDF-8 gene is a human GDF-8 gene.

4. An isolated GDF gene promoter comprising the nucleotide sequence of SEQ ID NO:2.

5. An isolated GDF gene promoter comprising the nucleotide sequence of SEQ ID NO:3.

6. An isolated GDF gene promoter consisting of the nucleotide sequence of SEQ ID NO:1.

7. An isolated GDF gene promoter consisting of the nucleotide sequence of SEQ ID NO:2.

8. An isolated GDF gene promoter consisting of the nucleotide sequence of SEQ ID NO:3.

9. An isolated GDF gene promoter comprising a nucleotide sequence which is at least 95% identical to the entire nucleotide sequence of SEQ ID NO:1.

10. An isolated GDF gene promoter comprising a nucleotide sequence which is at least 90% identical to the entire nucleotide sequence of SEQ ID NO:1.

11. An isolated GDF gene promoter comprising a nucleotide sequence which is at least 98% identical to the entire nucleotide sequence of SEQ ID NO:1.

12. A vector comprising the isolated GDF gene promoter of any one of claims 1, 4, 5, 9, 10, or 11.

13. The vector of claim 12, which is an expression vector.

14. A host cell transfected with the vector of claim 12.

* * * * *

SEQUENCE LISTING

<160> NUMBER OF SEQ ID NOS: 9

<210> SEQ ID NO 1
<211> LENGTH: 649
<212> TYPE: DNA
<213> ORGANISM: Homo sapiens

<400> SEQUENCE: 1

```
actagtatca taatcttaac ttttaattca ggtcttccta attttttattt tcctaattac      60
ttggcactaa aaataattta atacaacaaa taaaaatatt ttctacttca aatacttgcc     120
taaacaatat aaaatcattt tagtttttga ggaagtaata tttcatattt taaatatgta     180
gtataaatta aaattgactt atttaaatta caataagagt tgtgtgagga ttagtaagat     240
ttaagtacag tttatattat tgccaacata gacttttgtt tttcaaatgt cacaaatatc     300
ttttattatt tgtagattta tttctttttat gaagtagtca aatgaatcag ctcacccttg     360
actgtaacaa atactgctt ggtgacttgg gacagacagg gttttaacct ctgcagcga      420
gattcattgt ggagcaagag ccaatcatag atcctgacga cacttgtctc atctaagttg     480
gaatataaaa agccacttgg aatacagtat aaaagattca ctggtgtggc aagttgtctc     540
tcagactgta catgcattaa aattttgctt ggcattactc aaaagcaaaa gaaaagtaaa     600
aggaagaaac aagaacaaga aaaaagatta tattgatttt aaaatcatg               649
```

<210> SEQ ID NO 2
<211> LENGTH: 44
<212> TYPE: DNA
<213> ORGANISM: Homo sapiens

<400> SEQUENCE: 2

```
gagctttctt ttatgaagta gtcaaatgaa tcagctcacc cttg                      44
```

<210> SEQ ID NO 3
<211> LENGTH: 44
<212> TYPE: DNA
<213> ORGANISM: Homo sapiens

<400> SEQUENCE: 3

```
gagcgtttta acctctgaca gcgagattca ttgtggagca agag                      44
```

<210> SEQ ID NO 4
<211> LENGTH: 396
<212> TYPE: DNA
<213> ORGANISM: Mus musculus

<400> SEQUENCE: 4

```
gtacagttta tattagtaca cagacttcaa tttatcaaat gtcacatata tctttcatga      60
tttggggatt tatttcattt atgaagtagt caaatgaatc agcttgccct cgactgtaac     120
aaaatactgc ttggtgactt gtgacagaca gggttttaac ctctgacagc gagattcatt     180
gtggagcagg agccaatcat agatcctgac gacacttgtc tcctctaagt tggaatataa     240
aaagccactt ggaatacagt atacaggact ccctggcgtg gcaggttgtc tctcggacgg     300
tacatgcact aatatttcac ttggcattac tcaaaagcaa aagaagaaa taagaacaag     360
ggaaaaaaaa agattgtgct gatttttaaa atgatg                              396
```

<210> SEQ ID NO 5
<211> LENGTH: 799

```
<212> TYPE: DNA
<213> ORGANISM: Gallus gallus
<220> FEATURE:
<223> OTHER INFORMATION: AT POSITIONS
     9,30,32,50,55,92,114,146,149,151,154,158,AND 170 N
     CAN BE ANY NUCLEOTIDE

<400> SEQUENCE: 5
ttcggtatnt aatttgctgc ccaggatttn gntgacaaag gcaaactggn ttaanttaat    60
agggtccaca cttcagtaat gaattttgat antaaaggtc ccaatagtta gcanttatag   120
tcacacgtga acaaaatgtt tattcntgnt nacntagnac ntatcaggaa aacctatcat   180
gattttctga aatctgagct gcttaatgca cgtgaactgt tgaacagcat ggattcctcg   240
tgtttgcaat gtatttataa tgtattttt tccctcctc ctaacagaaa tccctcagaa    300
ttttccttga ggtagtacaa actttcagcc acaatagtga tagaatccta aggaaccct   360 aaaagagagc tctgcctcaa ttcatagtcc aactatgcgt tcagtgtata tttaagaatg   420
atagtgctgt cttccagcac tgctgcccat agtacttgga aatatatcct ttcagtatgt   480
gaagacgtat cctttacgaa gccaccatat aaatcagttc acccttggct gtaaccaaat   540
gctgtctagt gacttgtgat cgacagggct ttaacctctg acagctagat tcattgttgg   600
gacaacaacc aatcgtcggt tttgacgaca tgagcctaat caaagttgga gtataaaagc   660 cccccttggca tatataaggc acaccagtgt ggcaagccgt ctctcagatt gcatttgctg   720
tcacggatct gtttagaact gaaagaaaag gggaaaggga gagggggaa aaaagggcaa    780 aaagctgcag tgactgtaa                                                799

<210> SEQ ID NO 6
<211> LENGTH: 158
<212> TYPE: DNA
<213> ORGANISM: Homo sapiens

<400> SEQUENCE: 6
gaagtagtca aatgaatcag ctcacccttg actgtaacaa atactgctt ggtgacttgg    60 gacagacagg gttttaacct ctgacagcga gattcattgt ggagcaagag ccaatcatag   120
atcctgacga cacttgtctc atctaagttg aatataa                            158

<210> SEQ ID NO 7
<211> LENGTH: 158
<212> TYPE: DNA
<213> ORGANISM: Mus musculus

<400> SEQUENCE: 7
gaagtagtca aatgaatcag cttgccctcg actgtaacaa atactgctt ggtgacttgt    60 gacagacagg gttttaacct ctgacagcga gattcattgt ggagcaggag ccaatcatag   120
atcctgacga cacttgtctc ctctaagttg aatataa                            158

<210> SEQ ID NO 8
<211> LENGTH: 156
<212> TYPE: DNA
<213> ORGANISM: Sus scrofa

<400> SEQUENCE: 8
gaagtagtca aatgaatcag ctcacccttg actgtaacaa atactgttt ggtgacttgt    60 gacagacagg gttttaacct ctgacagcga gattcattgt ggagcaagag ccaatcatag   120
atcctgacga cacttgtctc atcaagtgga atataa                             156
```

-continued

```
<210> SEQ ID NO 9
<211> LENGTH: 159
<212> TYPE: DNA
<213> ORGANISM: Gallus gallus

<400> SEQUENCE: 9
gaagccagga tataaatcag ttcacccttg gctgtaacca aatgctgtct agtgacttgt      60
gatcgacagg gctttaacct ctgacagcta gattcattgt tgggacaaca accaatcgtc     120
ggttttgacg acatgagcct aatcaaagtt ggagtataa                            159
```